(12) United States Patent
Pellet-Rostaing et al.

(10) Patent No.: US 10,183,959 B2
(45) Date of Patent: Jan. 22, 2019

(54) COMPOUNDS WITH PHOSPHINE OXIDE AND AMINE FUNCTIONS, USEFUL AS URANIUM (VI) LIGANDS, AND USES THEREOF, IN PARTICULAR FOR EXTRACTING URANIUM(VI) FROM AQUEOUS SOLUTIONS OF SULPHURIC ACID

(71) Applicants: COMMISSARIAT À L'ÉNERGIE ATOMIQUE ET AUX ÉNERGIES ALTERNATIVES, Paris (FR); CENTRE NATIONAL DE LA RECHERCHE SCIENTIFIQUE, Paris (FR); UNIVERSITE DE MONTPELLIER, Montpellier (FR)

(72) Inventors: Stéphane Pellet-Rostaing, Villerubanne (FR); Antoine Leydier, Saint Etienne (FR); Guilhem Arrachart, Saint-Laurent-des-Arbres (FR); Raphaël Turgis, Le Grand Quevilly (FR); Véronique Dubois, Guajac (FR)

(73) Assignees: COMMISSARIAT À L'ÉNERGIE ATOMIQUE ET AUX ÉNERGIES ALTERNATIVES, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/564,053

(22) PCT Filed: Apr. 1, 2016

(86) PCT No.: PCT/EP2016/057264
§ 371 (c)(1),
(2) Date: Oct. 3, 2017

(87) PCT Pub. No.: WO2016/156591
PCT Pub. Date: Oct. 6, 2016

(65) Prior Publication Data
US 2018/0094009 A1 Apr. 5, 2018

(30) Foreign Application Priority Data
Apr. 3, 2015 (FR) ...................... 15 52886

(51) Int. Cl.
*C07F 9/00* (2006.01)
*C07F 9/53* (2006.01)
(Continued)

(52) U.S. Cl.
CPC .......... *C07F 9/5304* (2013.01); *C22B 3/0005* (2013.01); *C22B 60/026* (2013.01); *C22B 60/0243* (2013.01); *Y02P 10/234* (2015.11)

(58) Field of Classification Search
CPC . C07F 9/5304; C22B 60/026; C22B 60/0243; C22B 3/0005
(Continued)

(56) References Cited

U.S. PATENT DOCUMENTS 3,116,334 A * 12/1963 Buckler ................ C07F 7/28
568/15
3,442,948 A * 5/1969 Wiley ................ C07F 9/5004
564/15

(Continued)

FOREIGN PATENT DOCUMENTS

CN 104031088 A 9/2014
FR 2507172 * 12/1982

(Continued)

OTHER PUBLICATIONS

Search Report issued in French Patent Application No. 15 52886 dated Feb. 19, 2016.

(Continued)

*Primary Examiner* — Steven J Bos
(74) *Attorney, Agent, or Firm* — Pearne & Gordon LLP

(57) ABSTRACT

The invention relates to compounds which correspond to the general formula (I) below:

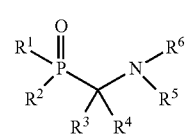

in which: $R^1$ and $R^2$ represent, independently of one another, a $C_4$ to $C_{12}$ acyclic hydrocarbon group; $R^3$ represents H; a $C_1$ to $C_{12}$ acyclic hydrocarbon group with optionally one or more heteroatoms; a $C_5$ or $C_6$ cyclic hydrocarbon group; or a 5- or 6-membered heterocyclic group; $R^4$ represents H or a $C_1$ to $C_{12}$ acyclic hydrocarbon group with optionally one or more heteroatoms; $R^5$ and $R^6$ represent, independently of one another, H; a $C_1$ to $C_{12}$ acyclic hydrocarbon group with optionally one or more heteroatoms; a $C_5$ or $C_6$ cyclic hydrocarbon group; or a 5- or 6-membered heterocyclic group; on the condition however that $R^5$ and $R^6$ do not each represent H.

The invention also relates to the uses of these compounds as uranium(VI) ligands, in particular for extracting uranium (VI) from an aqueous solution of sulphuric acid, and also to a method that makes it possible to recover the uranium(VI) present in an aqueous solution of sulphuric acid resulting from the attack of a uranium ore by sulphuric acid and using said the compounds.

21 Claims, 1 Drawing Sheet

(51) Int. Cl.
  *C22B 60/02* (2006.01)
  *C22B 3/26* (2006.01)
(58) Field of Classification Search
  USPC .................................................. 423/9, 10
  See application file for complete search history.

(56) References Cited

U.S. PATENT DOCUMENTS

2015/0133688 A1   5/2015   Arrachart
2016/0016150 A1   1/2016   El Mourabit

FOREIGN PATENT DOCUMENTS

WO   2013/167516 A1   11/2013
WO   2014/139869 A1    9/2014

OTHER PUBLICATIONS

International Preliminary Report on Patentability issued in Application No. PCT/EP2016/057264 dated Mar. 15, 2017.
International Search Report issued in Application No. PCT/EP2016/057264 dated Jul. 25, 2016.
Written Opinion issued in Application No. PCT/EP2016/057264 dated Jul. 25, 2016.
C.A. Blake et al., "Progress Report: Further Studies of the Dialkylphoshoric Acid Extraction (DAPEX) Process for Uranium" dated Dec. 18, 1956.
R.A.Cherkasov et al., "Acid-Base Properties of α-Aminomethylphosphine Oxides" ISSN 1070-3632, Russian Journal of General Chemistry, 2012, vol. 82, No. 9, pp. 1492-1503.
R.A.Cherkasov et al., "Membrane Transport of Metal Ions with Lipophilic Aminomethylphosphine Oxides" ISSN 1070-3632, Russian Journal of General Chemistry, 2011, vol. 81, No. 7, pp. 1464-1469.
C.F. Coleman et al., "Solvent Extraction with Alkyl Amines" Nuclear Technology, Industrial and Engineering Chemistry, vol. 50, No. 12, Dec. 1958.
A.R. Garifzyanov et al., "Membrane Extraction of Metal Ions by Aminophosphoryl Reagents in the Active Transport Conditions", ISSN 1070-3632, Russian Journal of General Chemistry, 2013, vol. 83, No. 2, pp. 267-273.
Edward Grzys et al., "Aminophosphonate-Induced Changes of Betacyanine and Ionic Efflux" Journal of Biosciences, vol. 56, No. 5/6, 2001.
Liudmila K. Kibardina et al., "Synthesis of Novel Macrocyclic Ligands Containing Phosphoryl and Aminoacetal Fragments" Phosphorus, Sulfur and Silicon and the Related Elements, vol. 188, No. 1-3, 2013.
Liliya I. Vagapova et al., "β- and γ-Amino Acetals Containing Phosphine Oxide Groups. Synthesis and Reactions with Resorcinol Derivatives" ISSN 1070-4280, Russian Journal of General Chemistry, 2014, vol. 50, No. 6, pp. 778-782.
Yalei Zhao et al., "Catalyst-Free and Selective C-N Bond Functionalization: Stereospecific Three-Component Coupling of Amines, Dichloromethane, and >P(O)H Species Affording α-Aminophosphorous Compounds" The Journal of Organic Chemistry, vol. 80, No. 1, 2015.
R.A. Cherkasov et al., New Aminophosphoryl Extractants for Liquid Extraction of Pt(IV) Ions, ISSN 1070-3632, Russian Journal of General Chemistry, 2010, vol. 80, No. 1, pp. 151-152.
Vagapova, Liliya I. et al. " Phosphorylated Aminoacetal in the Synthesis of New Acyclic, Cyclic, and Heterocyclic Polyphenol Structures" In: Heteroatom Chemistry; 2014, vol. 25, No. 3, pp. 185.
Kleszczynska, Halina et al. "The Hemolytic Toxicity of Some New Aminophosphonates" In: Cellular & Molecular Biology Letters; Jun. 10, 2001, vol. 6, pp. 271-275.
Wieczorek, J.S. et al. "Synthesis and Physiological Activities of New Acyclic Aminophosphonates" In: Phosphorus, Sulfur and Silicon; 2000, vol. 166, pp. 111-123.
Wieczorek, J.S. et al. "Synthesis of Some New Cyclic Aminophosphonates and Their Physiological Activities" In: Phosphorus, Sulfur and Silicon, 2001, vol. 174, pp. 119-128.

* cited by examiner

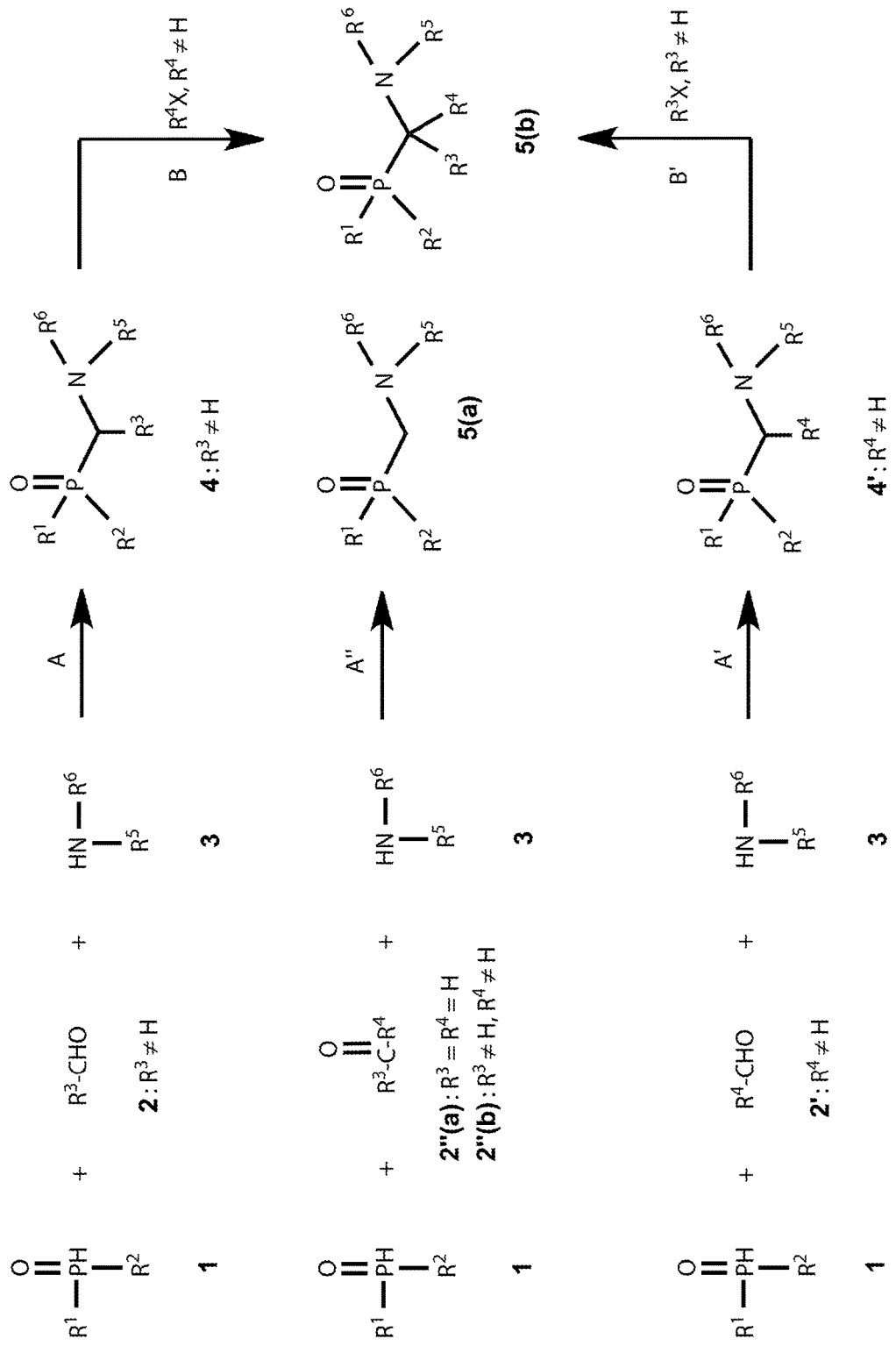

COMPOUNDS WITH PHOSPHINE OXIDE AND AMINE FUNCTIONS, USEFUL AS URANIUM (VI) LIGANDS, AND USES THEREOF, IN PARTICULAR FOR EXTRACTING URANIUM(VI) FROM AQUEOUS SOLUTIONS OF SULPHURIC ACID

TECHNICAL FIELD

The invention relates to the field of the extraction of uranium(VI) from aqueous media comprising sulphuric acid.

More specifically, the invention relates to novel bifunctional compounds, comprising both a phosphine oxide function and an amine function, which are capable of extracting alone (that is to say in the absence of any extractant compound) uranium(VI) from an aqueous solution of sulphuric acid, and to do so both very efficiently and with a high selectivity for uranium(VI).

The invention also relates to uses of these compounds as uranium(VI) ligands and, in particular, for extracting uranium(VI) from an aqueous solution of sulphuric acid such as a solution derived from the lixiviation of a uranium ore by sulphuric acid and which uses said compounds as extractants.

The invention finds application in particular in the treatment of uranium ores (uraninite, pitchblende, coffinite, brannerite, carnotite, etc.) with a view to upgrading the uranium present in said ores.

PRIOR ART

Uranium-bearing ores (or uranium ores) are extracted from mines, crushed and ground until the consistency of a fine sand is reached, then they are subjected to an attack, also called lixiviation, by sulphuric acid (except if their gangue is naturally alkaline, in which case this lixiviation would require a totally unacceptable consumption of sulphuric acid).

Sulphuric acid has been chosen for two reasons: on the one hand, it is the cheapest acid, this acid being able to be manufactured on-site in uranium ore treatment plants from sulphur by a so-called "double catalysis" method, and, on the other hand, its use leads to effluents that are relatively easy to treat because the sulphate ions may be to a large extent removed by precipitation with lime.

The attack of each uranium ore is studied on the basis of an optimisation of the uranium(VI) dissolution yield compared to the quantity of sulphuric acid consumed. Certain ores are easily attacked in a stirred vessel and only require around 25 kg of pure sulphuric acid per tonne of ore whereas others are only attacked in an autoclave and require more than 100 kg of pure sulphuric acid per tonne of ore.

In all cases, numerous other elements are also solubilised such as aluminium, iron and silica, which generally constitute the elements of the gangue, as well as elements that vary from one ore to the next, as much by their nature as by their quantity, such as molybdenum, titanium, zirconium, copper, nickel and arsenic.

After a filtration intended to remove insoluble materials, the aqueous solution derived from lixiviation by sulphuric acid, which generally contains 0.1 to 10 g/L of uranium(VI), is sent to a purification unit in which it is not only purified but also concentrated either by passage on ion exchange resins or by liquid-liquid extraction (that is to say by means of a solvent phase or organic phase). It then undergoes a pH adjustment and a precipitation, which makes it possible to obtain a yellow-coloured uranium concentrate which is commonly called "yellow cake".

This uranium concentrate is filtered, washed, dried, optionally calcinated (to obtain uranium sesquioxide $U_3O_8$), before being placed in drums and expedited to a refining-conversion plant in which the uranium is transformed into $UF_6$ of nuclear purity.

Two methodes are currently used to purify by liquid-liquid extraction the aqueous solution derived from lixiviation by sulphuric acid: the AMEX (from "AMine Extraction") method on the one hand, and the DAPEX (from "DiAlkylPhosphoric acid Extraction") method on the other hand.

The AMEX method (which is described by Coleman et al. in *Ind. Eng. Chem.* 1958, 50, 1756-1762, below reference [1]), uses, as extractant, a commercially available mixture of trialkylated tertiary amines of which the alkyl chains are $C_8$ to $C_{10}$, for example Adogen 364 or Alamine 336, in solution in a kerosene type hydrocarbon, optionally with a heavy alcohol ($C_{10}$ to $C_{13}$) added which plays the role of phase modifier, whereas the DAPEX method (which is described by Blake et al., *Oak Ridge National Laboratory Report*, 18 Dec. 1956, below reference [2]) uses, as extractant, a synergic mixture of di(2-ethylhexyl)phosphoric acid (HDEHP) and tri-n-butylphosphate (TBP), in a kerosene type hydrocarbon.

None of these methods is entirely satisfactory.

Indeed, apart from the selectivity for uranium(VI) of the mixture of tertiary amines used in the AMEX method which could be improved, in particular with regard to molybdenum, it turns out that, on the one hand, these amines are degraded during the method into secondary and primary amines by acid hydrolysis—which further reduces their selectivity for uranium(VI)—and that, on the other hand, the AMEX method leads to the formation of interfacial grime which perturbs the correct operation of the extractors in which it is implemented and which are responsible for extractant and phase modifier losses.

As for the DAPEX method, it has, for its part, the drawbacks of using an extractant that is even less selective for uranium(VI) than the mixture of tertiary amines used in the AMEX method, of having a slow extraction kinetic (unlike the AMEX method which has a quick extraction kinetic) and of drastically limiting the modalities of stripping of uranium(VI), once it is extracted from the aqueous solution derived from lixiviation by sulphuric acid.

The development of new extractants that are more efficient than those currently used in the AMEX and DAPEX methodes thus constitutes an important challenge for the uranium mining industry.

In particular, the supply of extractants that are capable of extracting uranium(VI) very efficiently from an aqueous solution of sulphuric acid while being more selective for uranium(VI) than the mixture of tertiary amines used in the AMEX method and less sensitive to acids than said tertiary amines would make it possible to obtain purer concentrates of uranium, which would facilitate as much the implementation of later methods of refining-conversion of these concentrates.

Recently, it has been proposed in WO-A-2014/139869 (below reference [3]) to extract uranium(VI) from an aqueous solution of sulphuric acid using, as extractants, compounds comprising both a phosphonic acid or phosphonate function and an amide function bound to each other by a methylene bridge of which one of the hydrogen atoms is optionally substituted by a hydrocarbon group.

These compounds notably include n-butyl 1-(N,N-di-2-ethylhexyl-carbamoyl)nonylphosphonate, noted DEHCNPB, which has a high affinity for uranium(VI) coupled with a selectivity for uranium(VI) with regard to molybdenum much greater than that of the Alamine 336 used in the AMEX method and, thus, a fortiori, than that of the HDEHP/TBP synergic mixture used in the DAPEX method.

However, considering that it should be possible to supply extractants even more efficient than those proposed in reference [3], the Inventors have set themselves the aim of developing a novel family of compounds that exhibit a selectivity for uranium(VI) that is even higher than that exhibited by the reference extractants [3] and, in particular, by DEHCNPB, without however losing affinity for uranium (VI).

DESCRIPTION OF THE INVENTION

This aim is attained by the invention which has, firstly, for object compounds which correspond to the general formula (I) below:

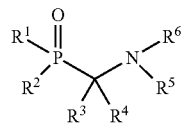

(I)

in which:
$R^1$ and $R^2$ represent, independently of one another, a saturated or unsaturated, acyclic hydrocarbon group comprising 4 to 12 carbon atoms;
$R^3$ represents a hydrogen atom; a saturated or unsaturated, acyclic hydrocarbon group comprising 1 to 12 carbon atoms and optionally one or more heteroatoms; a saturated or unsaturated, cyclic hydrocarbon group with 5 or 6 carbon atoms; or a saturated or unsaturated, 5- or 6-membered heterocyclic group;
$R^4$ represents a hydrogen atom or a saturated or unsaturated, acyclic hydrocarbon group comprising 1 to 12 carbon atoms and optionally one or more heteroatoms;
$R^5$ and $R^6$ represent, independently of one another, a hydrogen atom; a saturated or unsaturated, acyclic hydrocarbon group comprising 1 to 12 carbon atoms and optionally one or more heteroatoms; a saturated or unsaturated, cyclic hydrocarbon group with 5 or 6 carbon atoms; or a saturated or unsaturated, 5- or 6-membered heterocyclic group; on the condition however that $R^5$ and $R^6$ do not each represent a hydrogen atom.

Thus, the compounds according to the invention are characterised in that they comprise, on the one hand, a phosphine oxide function, and, on the other hand, an amine function, these functions being bound to each other by a methylene bridge of which the hydrogen atom(s) may be substituted.

In what precedes and in what follows:
"saturated or unsaturated, acyclic hydrocarbon group comprising 4 to 12 carbon atoms" is taken to mean any alkyl group comprising 1, 2, 3, 4, 5, 6, 7, 8, 9, 10, 11 or 12 carbon atoms, or any alkenyl or alkynyl group comprising 2, 3, 4, 5, 6, 7, 8, 9, 10, 11 or 12 carbon atoms, of which the chain is linear or branched;
"saturated or unsaturated, acyclic hydrocarbon group comprising 1 to 12 carbon atoms and optionally one or more heteroatoms" is taken to mean any saturated hydrocarbon group comprising 1, 2, 3, 4, 5, 6, 7, 8, 9, 10, 11 or 12 carbon atoms or any unsaturated hydrocarbon group comprising 2, 3, 4, 5, 6, 7, 8, 9, 10, 11 or 12 carbon atoms, of which the chain is linear or branched and may comprise in addition one or more heteroatoms (that is to say be interrupted by one or more heteroatoms) or be substituted by one or more heteroatoms or by one or more groups comprising one or more heteroatoms;
"heteroatom" is taken to mean any atom other than carbon and hydrogen, this atom being typically an atom of nitrogen, oxygen or sulphur;
"saturated or unsaturated, cyclic hydrocarbon group with 5 or 6 carbon atoms" is taken to mean any monocyclic, saturated or unsaturated group, of which the ring is formed of 5 or 6 carbon atoms; thus, this group may be a cycloalkyl, cycloalkenyl or cycloalkynyl group (for example, cyclopentyl, cyclohexyl, cyclopentenyl or cyclohexenyl), or instead an aromatic group (that is to say a group of which the ring meets the Hückel aromaticity rule and thus has a number of delocalised electrons $\pi$ equal to 4n+2, for example, phenyl or benzyl);
"saturated or unsaturated, 5- or 6-membered heterocyclic group" is taken to mean any monocyclic, saturated or unsaturated group, of which the ring is formed of 5 or 6 atoms of which one at least of these atoms is a heteroatom; thus, this group may be a saturated heterocyclic group (for example, tetrahydrofuryl, tetrahydrothiophenyl, pyrrolidinyl or piperidinyl), an unsaturated but non-aromatic heterocyclic group (for example, pyrrolinyl), or instead a heteroaromatic group (for example, furanyl, thiophenyl or pyrrolyl).

In accordance with the invention, in the general formula (I), $R^1$ and $R^2$, which may be identical or different, each advantageously represent a linear or branched alkyl group comprising 6 to 12 carbon atoms.

Even more, it is preferred that $R^1$ and $R^2$ are identical to each other and that they each represent a linear or branched alkyl group comprising 8 to 10 carbon atoms, such as an n-octyl, 2-methylheptyl, 2-ethylhexyl, 1,5-dimethylhexyl, 2,4,4-tri-methylpentyl, n-nonyl, 2-methyloctyl, 2-ethylheptyl, 1,2-dimethylheptyl, 2,6-di-methylheptyl, 3,5,5-trimethylhexyl, n-decyl, 2-methylnonyl, 3,7-dimethyloctyl, 2,4,6-trimethylheptyl or 2-butylhexyl group, n-octyl and 2-ethylhexyl groups being quite particularly preferred.

Furthermore, $R^3$ advantageously represents a linear or branched alkyl group comprising 1 to 12 carbon atoms.

Even more, it is preferred that $R^3$ represents a linear or branched alkyl group comprising 8 to 10 carbon atoms such as those cited beforehand, the 2,4,4-trimethylpentyl group being, in this case, quite particularly preferred.

$R^4$ advantageously represents, for its part, a hydrogen atom or a linear or branched alkyl group comprising 1 to 12 carbon atoms and, better still, 1 to 4 carbon atoms.

Even more, it is preferred that $R^4$ represents a hydrogen atom.

As for $R^5$ and $R^6$, which may be identical or different, they each advantageously represent a linear or branched alkyl group comprising 1 to 12 carbon atoms, or a cycloalkyl group.

Even more, it is preferred that $R^5$ and $R^6$ are identical to each other and that they represent a linear or branched alkyl group comprising 8 to 10 carbon atoms such as those cited beforehand—the 2-ethylhexyl and n-octyl groups being quite particularly preferred—or a cyclohexyl group.

Compounds that exhibit these characteristics are in particular:
- the compound designated below ODODEHANP, which corresponds to the general formula (I) in which $R^1$, $R^2$ and $R^3$ each represent an n-octyl group, $R^4$ represents a hydrogen atom and $R^5$ and $R^6$ each represent a 2-ethylhexyl group;
- the compound designated below ODODOANP, which corresponds to the general formula (I) in which $R^1$, $R^2$ and $R^3$ each represent an n-octyl group, $R^4$ represents a hydrogen atom and $R^5$ and $R^6$ each represent an n-octyl group;
- the compound designated below ODODEHATMHP, which corresponds to the general formula (I) in which $R^1$ and $R^2$ each represent a n-octyl group, $R^3$ represents a 2,4,4-trimethylpentyl group, $R^4$ represents a hydrogen atom and $R^5$ and $R^6$ each represent a 2-ethylhexyl group; and
- the compound designated below ODODOATMHP, which corresponds to the general formula (I) in which $R^1$ and $R^2$ each represent an n-octyl group, $R^3$ represents a 2,4,4-trimethylpentyl group, $R^4$ represents a hydrogen atom and $R^5$ and $R^6$ each represent an n-octyl group.

Among these compounds, the compound ODODEHATMPH is quite particularly preferred.

The compounds according to the invention may in particular be obtained by the synthesis routes that are described in appended FIG. 1.

These compounds have a particularly high affinity for uranium(VI) coupled with a high selectivity for this element with regard to other metal elements (iron, molybdenum, gadolinium, neodymium, zirconium, titanium, etc.).

In particular, they are capable of extracting uranium(VI) very efficiently from an aqueous solution of sulphuric acid and, in particular, from an aqueous solution comprising 0.01 mol/L to 2 mol/L of sulphuric acid.

Also, a further object of the invention is the use of the compounds according to the invention as uranium(VI) ligands and, in particular, for extracting uranium(VI) from an aqueous solution of sulphuric acid, said aqueous solution comprising, preferably, 0.01 mol/L to 2 mol/L of sulphuric acid.

Typically, the extraction of uranium(VI) from the aqueous solution of sulphuric acid is carried out by the liquid-liquid extraction technique, that is to say by contacting said aqueous solution with an organic phase comprising a compound of general formula (I) then by separating said aqueous solution from the organic phase, in which case the organic phase advantageously comprises the compound in solution, at a concentration of 0.01 mol/L to 0.25 mol/L, in an organic diluent, which is, preferably, a diluent of aliphatic type such as n-dodecane, hydrogenated tetrapropylene (HTP), kerosene or Isane (for example, that sold by the TOTAL Company under the trade name Isane IP-185).

In accordance with the invention, the aqueous solution from which the uranium(VI) is extracted is advantageously an aqueous solution of sulphuric acid which is derived from the lixiviation of a uranium ore by sulphuric acid, in which case this aqueous solution typically comprises 0.1 g/L to 8 g/L of uranium, 0.1 mol/L to 2 mol/L of sulphate ions and 0.01 mol/L to 2 mol/L of sulphuric acid.

The object of the invention is also a method for recovering the uranium present in an aqueous solution of sulphuric acid derived from the lixiviation of a uranium ore by sulphuric acid, which method comprises:
a) an extraction of uranium, in oxidation state VI, from the aqueous solution by contacting the aqueous solution with an organic phase comprising a compound as defined previously, then separating the aqueous solution from the organic phase; and
b) a stripping of uranium(VI) from the organic phase obtained at the end of step a) by contacting the organic phase with an aqueous solution comprising at least one carbonate, for example of ammonium or of sodium, then separating the organic phase from the aqueous solution.

In this method, the organic phase used at step a) advantageously comprises 0.01 mol/L to 0.25 mol/L of the compound in solution in an organic diluent, which is, preferably, of aliphatic type such as those previously cited.

The aqueous solution of sulphuric acid, which is used at step a), preferentially comprises 0.1 g/L to 8 g/L of uranium, 0.1 mol/L to 2 mol/L of sulphate ions and 0.01 mol/L to 2 mol/L of sulphuric acid, whereas the aqueous solution of carbonate(s), which is used at step b), preferentially comprises 0.1 mol/L to 1 mol/L of carbonate(s).

Step a) is, preferably, carried out at a temperature of 22-23° C. whereas step b) may be carried out at this temperature or hot, that is to say for example at a temperature of 30 to 45° C.

Furthermore, the volumetric ratio between the organic phase and the aqueous solution of sulphuric acid, which are used at step a), and/or the volumetric ratio between the organic phase and the aqueous solution of carbonate(s), which are used at step b), is (are) adjusted so that the aqueous solution obtained at the end of step b) has a uranium concentration which makes it possible to precipitate said uranium later in good conditions, that is to say a uranium concentration typically of 40 g/L to 100 g/L.

It is possible to favour a concentrating extraction (step a)) or, on the contrary, a concentrating stripping (step b)), or even an intermediate situation, each of these steps contributing to the concentration of uranium up to the targeted value.

Thus, the volumetric ratio between the organic phase and the aqueous solution of sulphuric acid may, for example, be less than or equal to 1 and, better still, comprised between 0.2 and 1, whereas the volumetric ratio between the organic phase and the aqueous solution of carbonate(s) may, for example, be greater than or equal to 1, to induce both a concentration of uranium in organic phase at step a) and a concentration of uranium in aqueous solution at step b).

In accordance with the invention, step a) of the method may comprise, in addition, the washing of the organic phase after its separation from the aqueous solution, to remove from this phase:
- either traces of acid capable of having been co-extracted with the uranium(VI), in which case said washing is, preferably, carried out by contacting the organic phase with an aqueous phase uniquely constituted of water, then separating the organic phase and the aqueous phase;
- or, depending on the required level of purity, traces of metal impurities co-extracted with uranium(VI), in which case said washing is, preferably, carried out by contacting the organic phase with an aqueous solution comprising a compound capable of complexing these impurities such as an oxalate or a citrate, for example of ammonium or sodium, then separating said organic phase and said aqueous solution.

The method may further comprise an acidification of the organic phase obtained at the end of step b) by contacting said organic phase with an aqueous acid solution, for example an aqueous solution of sulphuric acid, then separating the organic phase from the aqueous acid solution, with a view to its reuse for recovering the uranium(VI) present in another aqueous solution of sulphuric acid derived from the lixiviation of a uranium ore by sulphuric acid.

Other characteristics and advantages of the invention will become clearer on reading the complement to the description that follows and which relates to examples of synthesis of compounds according to the invention and the demonstration of the properties thereof and which is given in reference to the appended FIGURE.

Obviously, this complement to the description is only given to illustrate the object of the invention and does not constitute in any case a limitation of said object.

BRIEF DESCRIPTION OF THE FIGURE

FIG. 1 illustrates the different synthesis routes by which the compounds according to the invention may be synthesised.

DETAILED DESCRIPTION OF PARTICULAR EMBODIMENTS

Example I: Synthesis of Compounds According to the Invention

The compounds according to the invention may be synthesised by different synthesis routes as a function of the significations of $R^3$ and $R^4$.

These synthesis routes are illustrated in FIG. 1.

As this FIGURE shows, the compounds, which correspond to the general formula (I) in which one of $R^3$ and $R^4$ is different from a hydrogen atom whereas the other of $R^3$ and $R^4$ represents a hydrogen atom and which correspond to the compounds 4 and 4' of FIG. 1, may be obtained by a Kabachnik-Fields reaction which consists in condensing a dialkylphosphite oxide 1, of formula $R^1R^2P(O)H$, with, on the one hand, an aldehyde 2 of formula $R^3$—CHO in which $R^3$ is different from a hydrogen atom (reaction A in FIG. 1) or an aldehyde 2' of formula $R^4$—CHO in which $R^4$ is different from a hydrogen atom (reaction A' in FIG. 1) and, on the other hand, an amine 3 of formula $HNR^5R^6$, in the presence of para-toluene sulfonic acid in catalytic quantity in toluene.

Reactions A and A' are, for example, carried out by heating to reflux a mixture comprising n mmol of oxide 1, 1.2n mmol of aldehyde 2 (reaction A) or aldehyde 2' (reaction A') and 1.2n mmol of amine 3 in toluene (10n mL+50n mL to complete the Dean-Stark) with approximately 25n mg of para-toluene sulfonic acid (catalytic quantity) until at least 90% of oxide 1 are consumed, which is controlled by $^{31}P$ NMR. The solvent is next evaporated and the residue is purified by flash chromatography (Agilent Intelliflash 971-FP) on silica gel (eluent: cyclohexane/ethyl acetate 100-0/80-20, v/v) with monitoring by thin layer chromatography (TLC—Merck TLC Silica Gel 60 $F_{254}$) using phosphomolybdic acid in ethanol solution as stain.

The compounds, which correspond to the general formula (I) in which $R^3$ and $R^4$ are each a hydrogen atom and which correspond to the compounds 5(a) of FIG. 1, may be obtained by a reaction, also Kabachnik-Fields, noted A" in this FIGURE, that is carried out in the same manner as reactions A and A' but by replacing the aldehyde 2 or 2' by formaldehyde (compound 2"(a) of FIG. 1) which is introduced into the reaction medium in the form of paraformaldehyde.

Finally, the compounds, which correspond to the general formula (I) in which $R^3$ and $R^4$ are both different from a hydrogen atom and which correspond to the compounds 5(b) of FIG. 1, may be obtained:
either by a C-alkylation reaction of the compound 4, noted B in this FIGURE, that is carried out by means of a strong base such as sodium hydride, and a halide of formula $R^4$—X in which $R^4$ is different from a hydrogen atom, for example an iodide $R^4I$;
or by a C-alkylation reaction of the compound 4', noted B' in FIG. 1, that is also carried out by means of a strong base but by using a halide of formula $R^3$—X in which $R^3$ is different from a hydrogen atom, for example an iodide $R^{3'}$;
or instead by the aforesaid reaction A" but which is carried out using a ketone of formula $R^3$—C(O)—$R^4$ in which $R^3$ and $R^4$ are both different from a hydrogen atom (compound 2"(b) of FIG. 1) instead of formaldehyde.

Reactions B and B' are typically carried out by adding to a solution comprising (n mmol) of compound 4 (reaction B) or compound 4' (reaction B') in 1 M dimethylformamide (10n mL), under nitrogen and under stirring, a solution comprising 1.3n mmol of sodium hydride followed, 10 minutes after, by a solution comprising 1.5n mmol of the halide $R^4X$ (reaction B) or the halide $R^3X$ (reaction B'). The mixture is left to react for 18 hours under stirring then 25n mL of a solution of 1 M hydrochloric acid are added. The mixture is next extracted with 2×25n mL of ethyl ether. The organic phases are combined, washed successively with saturated (25n mL) sodium bicarbonate ($NaHCO_3$), with water (25n mL) and with brine (25n mL), then dried on magnesium sulphate ($MgSO_4$). After filtration and evaporation, the product is optionally purified by flash chromatography on silica gel.

The following compounds are thus synthesised.

I.2—Compound ODODEHANP:

The title compound, which corresponds to the general formula (I) in which $R^1=R^2=R^3$=n-octyl, $R^4$=H, $R^5=R^6$=2-ethylhexyl, is synthesised by implementing step A, from di-n-octylphosphine oxide (4.4 mmol), n-nonanal and di(2-ethylhexyl)amine (reflux for 24 hours at 140° C.).

Yield: 69% (3.2 mmol)

$^{31}P$ NMR (162 MHz, $CDCl_3$, 25° C.) δ (ppm): 53.0

$^1H$ NMR (400 MHz, $CDCl_3$, 25° C.) δ (ppm): 2.44 (m, $J_{P-H}$=8.4 Hz, 1H, P—CH(Oct)-N); 2.58 (m, 2H, N—$CH_2$—CH); 2.37 (m, 2H, N—$CH_2$—CH); 1.90 (m, 2H); 1.86-1.50 (m, 10H); 1.42-1.11 (m, 48H); 0.91-0.78 (m, 21H, $CH_3$)

$^{13}C$ NMR (100 MHz, $CDCl_3$, 25° C.) δ (ppm): 60.3 & 59.7 (d, $J_{C-P}$=66.7 Hz, P—CH—N); 57.2 (N—$CH_2$); 38.2 (CH—$CH_2$—N); 31.9; 31.4; 31.3; 31.2; 31.1; 29.9; 29.6; 29.5; 29.3; 29.1; 25.6; 24.5; 24.3; 24.1; 23.3; 23.1; 22.7; 22.1; 21.9 ($CH_2$); 14.1; 10.9; 10.7 ($CH_3$)

HR-ESI-MS: calculated for $C_{41}H_{87}NOP^+$=640.6525. found=640.6495.

I.3—Compound ODEHDEHANP:

The title compound, which corresponds to the general formula (I) in which $R^1=R^2$=2-ethylhexyl, $R^3$=n-octyl, $R^4$=H, $R^5=R^6$=2-ethylhexyl, is synthesised by implementing step A, from di(2-ethylhexyl)phosphine oxide (2.7 mmol), n-nonanal and di(2-ethylhexyl)amine (reflux for 8 hours at 140° C.).

Yield: 27% (0.65 mmol)

$^{31}P$ NMR (162 MHz, $CDCl_3$, 25° C.) δ (ppm): 51.6

$^1H$ NMR (400 MHz, $CDCl_3$, 25° C.) δ (ppm): 2.84 (m, 2H, P—CH(CH($C_2H_5$)—$C_6H_{13}$)—N); 2.34 (m, 2H); 1.88-

1.07 (m, 55H); 0.92-0.78 (m, 27H, $CH_3$) HR-ESI-MS: calculated for $C_{41}H_{87}NOP^+$=640.6525. found=640.6513.

I.4—Compound ODODOANP:

The title compound, which corresponds to the general formula (I) in which $R^1=R^2=R^3$=n-octyl, $R^4$=H, $R^5=R^6$=n-octyl, is synthesised by implementing step A, from di-n-octylphosphine oxide (7.7 mmol), n-nonanal and di-n-octylamine (reflux for 24 hours at 140° C.).

Yield: 57% (4.4 mmol)

$^{31}P$ NMR (162 MHz, $CDCl_3$, 25° C.) δ (ppm): 53

$^1H$ NMR (400 MHz, $CDCl_3$, 25° C.) δ (ppm): 2.75 (m, $J_{P-H}$=7.6 Hz, 1H, P—CH(Oct)-N); 2.64 (m, 2H, N—$CH_2$); 2.49 (m, 2H, N—$CH_2$); 1.82-1.14 (m, 66H); 0.92-0.78 (m, 15H, $CH_3$)

$^{13}C$ NMR (100 MHz, $CDCl_3$, 25° C.) δ (ppm): 60.7 & 60.0 (d, $J_{C-P}$=66.7 Hz, P—CH—N); 53.2 (N—$CH_2$); 32.1; 31.7, 31.6; 31.5; 30.1; 29.9; 29.8; 29.6; 29.5; 29.3; 27.6; 27.1; 27.0; 26.3; 25.3; 22.9; 22.2 ($CH_2$); 14.3 ($CH_3$)

HR-ESI-MS: calculated for $C_{41}H_{87}NOP^+$=640.6525. found=640.6523.

I.5—Compound ODODEHATMHP:

The title compound, which corresponds to the general formula (I) in which $R^1=R^2$=n-octyl, $R^3$=2,4,4-trimethylpentyl, $R^4$=H, $R^5=R^6$=2-ethylhexyl, is synthesised by implementing step A, from di-n-octylphosphine oxide (7.6 mmol), 3,5,5-trimethylhexanal and di(2-ethylhexyl)amine (reflux for 72 hours at 140° C.).

Yield: 72% (5.5 mmol)

$^{31}P$ NMR (162 MHz, $CDCl_3$, 25° C.) δ (ppm): 52.9

$^1H$ NMR (400 MHz, $CDCl_3$, 25° C.) δ (ppm): 2.87 (m, $J_{P-H}$=8.4 Hz, 1H, P—CH(Oct)-N); 2.68 (m, 2H, N—$CH_2$—CH); 2.38 (m, 2H, N—$CH_2$—CH); 1.87-1.51 (m, 10H); 1.48-1.08 (m, 41H); 0.96-0.79 (m, 30H, $CH_3$)

$^{13}C$ NMR (100 MHz, $CDCl_3$, 25° C.) δ (ppm): 57.6 & 56.9 (d, $J_{C-P}$=65.3 Hz, P—CH—N); 52.5; 52.2 (N—$CH_2$); 39.1; 38.5; 38.4; 38.2; 28.0; 27.5; 22.4 (CH); 36.8; 36.5; 35.9; 34.9; 32.0; 31.8; 31.4; 31.2; 28.0; 27.5; 24.7; 24.4; 23.5; 22.8; 22.1 ($CH_2$); 30.6; 30.5; 21.8; 21.7; 14.3; 14.2; 11.1; 11.0; 10.9 ($CH_3$)

HR-ESI-MS: calculated for $C_{41}H_{87}NOP^+$=640.6525. found=640.6517.

I.6—Compound ODODOATMHP:

The title compound, which corresponds to the general formula (I) in which $R^1=R^2$=n-octyl, $R^3$=2,4,4-trimethylpentyl, $R^4$=H, $R^5=R^6$=n-octyl, is synthesised by implementing step A, from di-n-octylphosphine oxide (7.5 mmol), 3,5,5-trimethylhexanal and di-n-octylamine (reflux for 72 hours at 140° C.).

Yield: 65% (4.92 mmol)

$^{31}P$ NMR (162 MHz, $CDCl_3$, 25° C.) δ (ppm): 53.5

$^1H$ NMR (400 MHz, $CDCl_3$, 25° C.) δ (ppm): 2.89-2.39 (m, 5H); 1.88-1.51 (m, 10H); 1.45-1.18 (m, 47H); 0.95-0.80 (m, 24H, $CH_3$)

$^{13}C$ NMR (100 MHz, $CDCl_3$, 25° C.) δ (ppm): 58.1 & 57.3; 57.7 & 57.0 (d, $J_{C-P}$=75.4 Hz, P—CH—N); 53.1 (N—$CH_2$); 52.5; 51.6 ($CH_2$—P); 27.9; 27.3; 22.1 (CH) 35.8; 34.7, 32.1; 31.7; 31.6; 31.5; 30.1; 29.9; 29.6; 29.4; 29.3; 27.6; 22.8; 22.2 ($CH_2$); 30.6; 30.3; 22.7; 14.3 ($CH_3$)

HR-ESI-MS: calculated for $C_{41}H_{87}NOP^+$=640.6525. found=640.6526.

I.7—Compound ODCHDOANP:

The title compound, which corresponds to the general formula (I) in which $R^1=R^2$=n-octyl, $R^3$=2,4,4-trimethylpentyl, $R^4$=H, $R^5=R^6$=cyclohexyl, is synthesised by implementing step A, from di-n-octylphosphine oxide (7.6 mmol), 3,5,5-trimethylhexanal and dicyclohexylamine (reflux for 96 hours at 140° C.).

Yield: 24% (1.9 mmol)

$^{31}P$ NMR (162 MHz, $CDCl_3$, 25° C.) δ (ppm): 53.5 & 50.4

$^1H$ NMR (400 MHz, $CDCl_3$, 25° C.) δ (ppm): 3.17-3.03 (m, $J_{P-H}$=12 Hz, 1H, P—CH(triMePent)-N); 2.68 (m, 2H, N—CH—$CH_2$); 1.97 (m, 1H); 1.85 (m, 2H); 1.77-1.53 (m, 18H); 1.39-1.15 (m, 32H); 0.92-0.82 (m, 18H, $CH_3$)

$^{13}C$ NMR (100 MHz, $CDCl_3$, 25° C.) δ (ppm): 57.1 & 56.2 (broad d, $J_{C-P}$=86 Hz, P—CH—N); 54.2; 54.1; 53.6; 53.5 (N—CH); 53.1; 53.0 ($CH_2$—P); 27.3; 22.4 (CH); 41.5; 41.4; 39.2; 39.1; 35.1; 34.8; 34.4; 32.0; 31.5; 31.4; 29.9; 28.5; 27.6; 27.5; 27.3; 27.1; 26.9; 26.7; 26.1; 22.8; 22.5; 22.3 ($CH_2$); 30.5; 22.2; 14.2 ($CH_3$)

HR-ESI-MS: calculated for $C_{37}H_{75}NOP^+$=580.5586. found=580.5582.

Example II: Properties of the Compounds According to the Invention

II.1—Capacity of the Compounds According to the Invention to Extract Uranium(VI) from a Synthetic Aqueous Solution with 10 Metal Elements in Sulphuric Acid:

The capacity of the compounds according to the invention to extract uranium(VI) from an aqueous solution of sulphuric acid is firstly tested on a synthetic aqueous solution, which comprises 10 metal elements (to keep as close as possible to the conditions encountered during the extraction of uranium(VI) from the liquor of lixiviation of uranium ores by sulphuric acid), and compared to that which exhibits, under the same experimental conditions, tri-n-octylamine (which is one of the two tertiary amines constituting the Alamine 336 used in the AMEX method) one the one, and HDEHP (which is one of the two extractants of the synergic mixture used in the DAPEX method) on the other hand).

The synthetic aqueous solution used within the scope of these tests comprises 250 mg/L of each of the following metal elements: uranium(VI), iron(III), molybdenum(VI), cerium(III), lanthanum(III), gadolinium(III), ytterbium(III), neodymium(III), titanium(IV) and zirconium(IV), 1 mol/L of $H_2SO_4$ and 1 mol/L of $Li_2SO_4$.

The compounds according to the invention tested are ODODEHANP, ODODOANP, ODODEHATMHP and ODODOATMHP.

The extraction tests are carried out, in tubes, by placing a volume of 1 to 2 mL of the synthetic aqueous solution in contact with an identical volume of an organic solution comprising either one of the tested compounds according to the invention or tri-n-octylamine or instead HDEHP at a level of 0.1 mol/L in n-dodecane, for 1 hour, under stirring and at a temperature of 21-22° C. After which, the aqueous and organic phases are separated from each other by gravity decantation in less than 3 minutes.

The concentrations of uranium and the other metal elements are measured by inductively coupled plasma optical emission spectrometry (ICP-OES):

in the synthetic solution before it is placed in contact with the organic solutions but after dilution to bring its uranium and iron concentrations to measurable values (0 to 20 ppm); and in the aqueous phases once separated from the organic phases, also after dilution of said aqueous phases.

The results of these tests are shown in table I below, in which are indicated the chemical structures of the different compounds tested, the distribution coefficients of uranium, iron, molybdenum, cerium, lanthanum, gadolinium, ytterbium, neodymium, titanium and zirconium, respectively noted $D_U$, $D_{Fe}$, $D_{Mo}$, $D_{Ce}$, $D_{La}$, $D_{Gd}$, $D_{Yb}$, $D_{Nd}$, $D_{Zr}$ and $D_{Ti}$, obtained with the extraction for tri-n-octylamine (for which the values of the distribution coefficients are given in italics and for information purposes, given the appearance of a third phase), HDEHP and for each of the tested compounds according to the invention as well as the potential formation of a third phase at extraction.

iron, cerium, lanthanum, gadolinium, ytterbium and neodymium are not at all extracted whereas molybdenum, zirconium and titanium are only extracted very weakly.

As an example, table II below presents the improvements obtained in terms of $D_U$, separation factor of uranium and iron, noted $FS_{U/Fe}$, separation factor of uranium and molyb-

TABLE I

| Compounds tested | $D_u$ | $D_{Fe}$ | $D_{Mo}$ | $D_{Ce}$ | $D_{La}$ | $D_{Gd}$ | $D_{Yb}$ | $D_{Nd}$ | $D_{Zr}$ | $D_{Ti}$ |
|---|---|---|---|---|---|---|---|---|---|---|
| PRIOR ART | | | | | | | | | | |
| 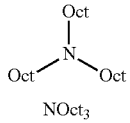 NOct₃ | *0.7* | *0* | *7* | *0* | *0* | *0* | *0* | *0* | *0.5* | *0* |
| | | | | | Third phase at extraction | | | | | |
| 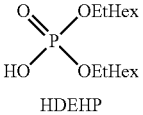 HDEHP | 6 | 0.2 | 70 | 0 | 0 | 0 | 2.4 | 0 | 120 | 14 |
| COMPOUNDS ACCORDING TO THE INVENTION | | | | | | | | | | |
| 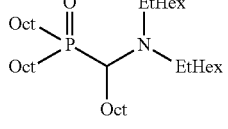 ODODEHANP | 90 | 0 | 1.4 | 0 | 0 | 0 | 0 | 0 | 0.3 | 0.1 |
| 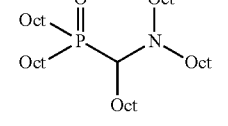 ODODOANP | >200 | 0 | 2.2 | 0 | 0 | 0 | 0 | 0 | 1.2 | 0.1 |
| 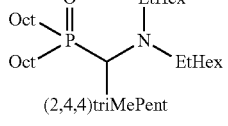 ODODEHATMHP | >200 | 0 | 0.6 | 0 | 0 | 0 | 0 | 0 | 0.1 | 0 |
| 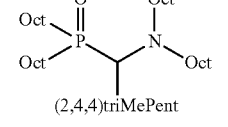 ODODOATMHP | >200 | 0 | 2.2 | 0 | 0 | 0 | 0 | 0 | 1.0 | 0.1 |

Oct = n-octyl; EtHex = 2-ethylhexyl; (2,4,4)triMePent = 2,4,4-trimethylpentyl

This table shows that the compounds according to the invention have a capacity to extract uranium(VI) from an aqueous solution of sulphuric acid distinctly higher that that exhibited by the reference extractants of the prior art.

It also shows that the compounds according to the invention exhibit in addition a selectivity for uranium(VI) with regard to the other metal elements much greater than that exhibited by the reference extractants of the prior art. Thus, denum, noted $FS_{U/Mo}$, separation factor of uranium and zirconium, noted $FS_{U/Zr}$, and separation factor of uranium and titanium, noted $FS_{U/Ti}$, with the compound ODODE-HATMHP compared to the reference extractants of the prior art (for tri-n-octylamine, the values are, here again, given in italics and for information purposes, given the appearance of a third phase).

TABLE II

|  |  | $D_U$ | $FS_{U/Fe}$ | $FS_{U/Mo}$ | $FS_{U/Zr}$ | $FS_{U/Ti}$ |
|---|---|---|---|---|---|---|
| Compounds tested | ODODEHATMHP | >200 | 9000 | 3300 | 1600 | 5400 |
|  | NOct$_3$ | 0.7 | 1300 | 0.1 | 1.5 | 1200 |
|  | Improvement | >250 | 7 | >10000 | 1000 | 4.5 |
|  | HDEHP | 6 | 36 | 0.09 | 0.04 | 0.5 |
|  | Improvement | >30 | 250 | >10000 | >10000 | >10000 |

This table shows that the improvements obtained are very high.

The possibility of recovering quantitatively in aqueous phase the uranium(VI) having been extracted by the compounds according to the invention is also tested.

To do so, the organic phases obtained at the end of the extraction tests are placed in contact, in tubes, volume to volume, with an aqueous solution comprising 0.5 mol/L of ammonium carbonate $(NH_4)_2CO_3$ and/or 0.5 mol/L of ammonium oxalate $((NH_4)_2C_2O_4)$. Contact is maintained for 1 hour, under stirring and at a temperature of 21-22° C. After which, the aqueous and organic phases are separated from each other by gravity decantation in less than 3 minutes and the aqueous phases are subjected to an analysis by plasma torch optical emission spectroscopy (ICP-OES) to measure the uranium concentration thereof.

These stripping tests show that an aqueous solution of a carbonate, such as ammonium carbonate, makes it possible to strip from an organic phase comprising a compound according to the invention the totality of the uranium(VI) having been extracted in this phase. It is thus possible to recover quantitatively in aqueous phase the uranium having been extracted using a compound according to the invention as extractant.

II.2—Comparison of the Extractant Properties of a Compound According to the Invention with Those of the Compound DEHCNPB of Reference [3]:

An extraction test is carried out to compare the extractant properties of a compound according to the invention, namely the compound ODODEHATMPH given its performances, with those exhibited by the compound DEHCNPB described in reference [3].

This test is carried out using:
- as aqueous phase: a synthetic aqueous solution comprising 200 mg/L of each of the following 7 metal elements: uranium(VI), iron(III), molybdenum(VI), gadolinium(III), neodymium(III), titanium(IV) and zirconium(IV), 1 mol/L of $H_2SO_4$ and 1 mol/L of $Li_2SO_4$; and
- as organic phases: solutions comprising 0.1 mol/L of the compound ODODEHATMPH or the compound DEHCNPB in n-dodecane.

A volume of the aqueous phase is placed in contact with an identical volume of each of the organic phases for 1 hour, under stirring and at a temperature of 21-22° C., then separated from this phase by gravity decantation.

The concentrations of uranium and other metal elements are measured by inductively coupled plasma atomic emission spectroscopy (ICP-OES) in the aqueous phase before and after contact with the organic phases.

The results of this test are presented in table III below, in which are indicated the distribution coefficients, noted $D_M$, of uranium, iron, molybdenum, gadolinium, neodymium, titanium and zirconium, as well as the separation factors, noted $FS_{U/M}$, obtained for each of the two compounds tested.

TABLE III

|  | Compounds tested | | | |
|---|---|---|---|---|
|  | ODODEHATMHP | | DEHCNPB | |
| Metal elements | $D_M$ | $FS_{U/M}$ | $D_M$ | $FS_{U/M}$ |
| Uranium | >200 | — | >200 | — |
| Iron | 0 | — | 0 | — |
| Molybdenum | 0.6 | >300 | 80 | >2.5 |
| Gadolinium | 0 | — | 0 | — |
| Neodymium | 0 | — | 0 | — |
| Zirconium | 0.1 | >2000 | 80 | >2.5 |
| Titanium | 0 | — | 15 | >13 |

This table shows that the objective pursued by the Inventors is indeed attained by the invention since the compounds according to the invention, while having an affinity for uranium(VI) comparable to that of the compound DEHCNPB ($D_U$>200), have a selectivity for uranium(VI) with regard to molybdenum, titanium and zirconium—which represent the main metal impurities capable of being extracted, jointly with uranium(VI), from an aqueous solution of sulphuric acid derived from the lixiviation of a uranium ore by sulphuric acid—very significantly greater than that shown by the compound DEHCNPB.

REFERENCES CITED

[1] Coleman et al., *Ind. Eng. Chem.* 1958, 50, 1756-1762
[2] Blake et al., *Oak Ridge National Laboratory Report,* 18 Dec. 1956
[3] WO-A-2014/139869

The invention claimed is:
1. A method for extracting uranium(VI) from an aqueous solution of sulphuric acid, comprising contacting the aqueous solution with an organic solution comprising a compound of formula (I):

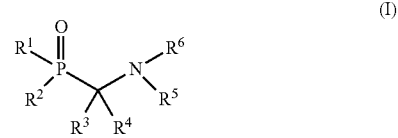

in which:
$R^1$ and $R^2$ represent, independently of one another, a saturated or unsaturated, acyclic hydrocarbon group comprising 4 to 12 carbon atoms;
$R^3$ represents a hydrogen atom; a saturated or unsaturated, acyclic hydrocarbon group comprising 1 to 12 carbon atoms and optionally one or more heteroatoms; a saturated or unsaturated, cyclic hydrocarbon group with 5 or 6 carbon atoms; or a saturated or unsaturated, 5- or 6-membered heterocyclic group;

$R^4$ represents a hydrogen atom or a saturated or unsaturated, acyclic hydrocarbon group comprising 1 to 12 carbon atoms and optionally one or more heteroatoms;

$R^5$ and $R^6$ represent, independently of one another, a hydrogen atom; a saturated or unsaturated, acyclic hydrocarbon group comprising 1 to 12 carbon atoms and optionally one or more heteroatoms; a saturated or unsaturated, cyclic hydrocarbon group with 5 or 6 carbon atoms; or a saturated or unsaturated, 5- or 6-membered heterocyclic group; wherein $R^5$ and $R^6$ do not each represent a hydrogen atom;

and then separating the aqueous solution from the organic solution.

2. The method of claim 1, in which $R^1$ and $R^2$ each represent a linear or branched alkyl group comprising 6 to 12 carbon atoms.

3. The method of claim 2, in which $R^1$ and $R^2$ are identical to each other and each represent a linear or branched alkyl group comprising 8 to 10 carbon atoms.

4. The method of claim 1, in which $R^3$ represents a linear or branched alkyl group comprising 1 to 12 carbon atoms.

5. The method of claim 1, in which $R^4$ represents a hydrogen atom or a linear or branched alkyl group comprising 1 to 12 carbon atoms.

6. The method of claim 1, in which $R^5$ and $R^6$ each represent a linear or branched alkyl group comprising 1 to 12 carbon atoms, or a cycloalkyl group.

7. The method of claim 1, in which:
$R^1$, $R^2$ and $R^3$ each represent an n-octyl group, $R^4$ represents a hydrogen atom and $R^5$ and $R^6$ each represent a 2-ethylhexyl group; or
$R^1$ and $R^2$ each represent a 2-ethylhexyl group, $R^3$ represents an n-octyl group, $R^4$ represents a hydrogen atom and $R^5$ and $R^6$ each represent a 2-ethylhexyl group; or
$R^1$, $R^2$ and $R^3$ each represent an n-octyl group, $R^4$ represents a hydrogen atom and $R^5$ and $R^6$ each represent an n-octyl group; or
$R^1$ and $R^2$ each represent an n-octyl group, $R^3$ represents a 2,4,4-trimethylpentyl group, $R^4$ represents a hydrogen atom and $R^5$ and $R^6$ each represent an n-octyl group; or
$R^1$ and $R^2$ each represent an n-octyl group, $R^3$ represents a 2,4,4-trimethylpentyl group, $R^4$ represents a hydrogen atom and $R^5$ and $R^6$ each represent a 2-ethylhexyl group.

8. The method of claim 1, in which the aqueous solution comprises 0.01 mol/L to 2 mol/L of sulphuric acid.

9. The method of claim 1, in which the organic solution comprises 0.01 mol/L to 0.25 mol/L of the compound in an organic diluent.

10. The method of claim 1, in which the aqueous solution is derived from the lixiviation of a uranium ore by sulphuric acid.

11. A method for recovering the uranium present in an aqueous solution of sulphuric acid derived from the lixiviation of a uranium ore by sulphuric acid, comprising:
a) an extraction of uranium, in oxidation state VI, from the aqueous solution, the extraction comprising contacting the aqueous solution with an organic phase comprising a compound of formula (I):

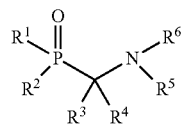

(I)

in which:
$R^1$ and $R^2$ represent, independently of one another, a saturated or unsaturated, acyclic hydrocarbon group comprising 4 to 12 carbon atoms;
$R^3$ represents a hydrogen atom; a saturated or unsaturated, acyclic hydrocarbon group comprising 1 to 12 carbon atoms and optionally one or more heteroatoms; a saturated or unsaturated, cyclic hydrocarbon group with 5 or 6 carbon atoms; or a saturated or unsaturated, 5- or 6-membered heterocyclic group;
$R^4$ represents a hydrogen atom or a saturated or unsaturated, acyclic hydrocarbon group comprising 1 to 12 carbon atoms and optionally one or more heteroatoms;
$R^5$ and $R^6$ represent, independently of one another, a hydrogen atom; a saturated or unsaturated, acyclic hydrocarbon group comprising 1 to 12 carbon atoms and optionally one or more heteroatoms; a saturated or unsaturated, cyclic hydrocarbon group with 5 or 6 carbon atoms; or a saturated or unsaturated, 5- or 6-membered heterocyclic group; wherein $R^5$ and $R^6$ do not each represent a hydrogen atom; then separating the aqueous solution from the organic phase; and
b) a stripping of uranium(VI) from the organic phase obtained at the end of a), the stripping comprising contacting the organic phase with an aqueous solution comprising at least one carbonate, then separating the organic phase from the aqueous solution.

12. The method of claim 11, in which the organic phase of a) comprises 0.01 mol/L to 0.25 mol/L of the compound in solution in an organic diluent.

13. The method of claim 11, in which the aqueous solution of sulphuric acid comprises 0.1 g/L to 8 g/L of uranium, 0.1 mol/L to 2 mol/L of sulphate ions and 0.01 mol/L to 2 mol/L of sulphuric acid.

14. The method of claim 11, in which:
a volumetric ratio between the organic phase and the aqueous solution of sulphuric acid less than or equal to 1 is used at a); and/or
a volumetric ratio between the organic phase and the aqueous solution of carbonate greater than or equal to 1 is used at b).

15. A compound of formula (I):

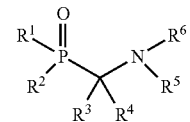

(I)

in which:
$R^1$ and $R^2$ represent, independently of one another, a saturated or unsaturated, acyclic hydrocarbon group comprising 4 to 12 carbon atoms;
$R^3$ represents a saturated or unsaturated, acyclic hydrocarbon group comprising 1 to 12 carbon atoms and optionally one or more heteroatoms; a saturated or unsaturated, cyclic hydrocarbon group with 5 or 6 carbon atoms; or a saturated or unsaturated, 5- or 6-membered heterocyclic group;
$R^4$ represents a hydrogen atom or a saturated or unsaturated, acyclic hydrocarbon comprising 1 to 12 carbon atoms and optionally one or more heteroatoms;
$R^5$ and $R^6$ represent, independently of one another, a hydrogen atom; a saturated or unsaturated, acyclic hydrocarbon group comprising 1 to 12 carbon atoms and optionally one or more heteroatoms; a saturated or unsaturated, cyclic hydrocarbon group with 5 or 6 carbon atoms; or a saturated or unsaturated, 5- or 6-membered heterocyclic group; wherein $R^5$ and $R^6$ do not each represent a hydrogen atom.

16. The compound of claim 15, in which $R^1$ and $R^2$ each represent a linear or branched alkyl group comprising 6 to 12 carbon atoms.

17. The compound of claim 16, in which $R^1$ and $R^2$ are identical to each other and each represent a linear or branched alkyl group comprising 8 to 10 carbon atoms.

18. The compound of claim 15, in which $R^3$ represents a linear or branched alkyl group comprising 1 to 12 carbon atoms.

19. The compound of claim 15, in which $R^4$ represents a hydrogen atom or a linear or branched alkyl group comprising 1 to 12 carbon atoms.

20. The compound of claim 15, in which $R^5$ and $R^6$ each represent a linear or branched alkyl group comprising 1 to 12 carbon atoms, or a cycloalkyl group.

21. The compound of claim 15, in which:

$R^1$, $R^2$ and $R^3$ each represent an n-octyl group, $R^4$ represents a hydrogen atom and $R^5$ and $R^6$ each represent a 2-ethylhexyl group; or $R^1$ and $R^2$ each represent a 2-ethylhexyl group, $R^3$ represents an n-octyl group, $R^4$ represents a hydrogen atom and $R^5$ and $R^6$ each represent a 2-ethylhexyl group; or $R^1$, $R^2$ and $R^3$ each represent an n-octyl group, $R^4$ represents a hydrogen atom and $R^5$ and $R^6$ each represent an n-octyl group; or $R^1$ and $R^2$ each represent an n-octyl group, $R^3$ represents a 2,4,4-trimethylpentyl group, $R^4$ represents a hydrogen atom and $R^5$ and $R^6$ each represent an n-octyl group; or $R^1$ and $R^2$ each represent an n-octyl group, $R^3$ represents a 2,4,4-trimethylpentyl group, $R^4$ represents a hydrogen atom and $R^5$ and $R^6$ each represent a 2-ethylhexyl group.

* * * * *